United States Patent
Tokizawa et al.

[11] Patent Number: 5,939,448
[45] Date of Patent: Aug. 17, 1999

[54] TRIAZOLE DERIVATIVE OR SALT THEREOF

[75] Inventors: Minoru Tokizawa, Narita; Sunao Takeda, Ichihara; Yasushi Kaneko, Narita; Hiromichi Eto; Kazuya Ishida, both of Narita; Kazunori Maebashi, Narashino; Masaru Matsumoto, Tomisato; Takemitsu Asaoka; Susumu Sato, both of Narita; Hideaki Matsuda, Abiko, all of Japan

[73] Assignee: SS Pharmaceutical Co., Ltd., Tokyo, Japan

[21] Appl. No.: 08/872,159

[22] Filed: Jun. 10, 1997

[30] Foreign Application Priority Data

Jun. 21, 1996 [JP] Japan .................................. 8-161760

[51] Int. Cl.$^6$ ...................... A61K 31/41; C07D 249/08
[52] U.S. Cl. ........................... 514/383; 548/268.6
[58] Field of Search .................. 514/383; 548/268.6

[56] References Cited

U.S. PATENT DOCUMENTS

| 4,999,429 | 3/1991 | Stahly . | |
|---|---|---|---|
| 5,147,886 | 9/1992 | Tokizawa et al. | 514/383 |
| 5,605,921 | 2/1997 | Imaizumi et al. | 514/383 |

FOREIGN PATENT DOCUMENTS

| 0 113 640 | 7/1984 | European Pat. Off. . |
|---|---|---|
| 0 415 320 | 3/1991 | European Pat. Off. . |
| 0 435 081 | 7/1991 | European Pat. Off. . |

OTHER PUBLICATIONS

Burger, "Medicinal Chemistry" 2nd Ed. NY (1960) p. 1055.
Xia et al, "Synthesis of new antifungal agents, etc" CA 123:55778, 1995.

*Primary Examiner*—Patricia L. Morris
*Attorney, Agent, or Firm*—Oblon, Spivak, McClelland, Maier & Neustadt, P.C.

[57] ABSTRACT

Described is a triazole derivative represented by the formula (1):

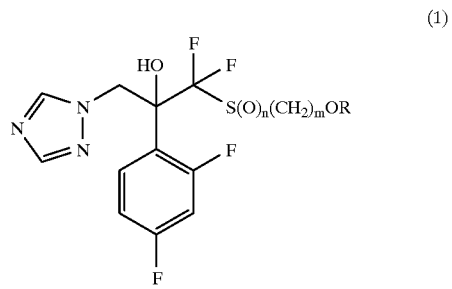

wherein R represents a hydrogen atom, an alkyl group, an aralkyl group or an acyl group, n stands for 0 to 2 and m stands for 1 to 5 or salt thereof, and a pharmaceutical containing the derivative or salt as an effective ingredient.

8 Claims, No Drawings

TRIAZOLE DERIVATIVE OR SALT THEREOF

BACKGROUND OF THE INVENTION

1. Field of the Invention

This invention relates to a triazole derivative or salt thereof which has excellent antimycotic activity and high safety, an intermediate for the preparation of the derivative or salt and a pharmaceutical comprising the same as an effective ingredient.

2. Description of the Related Art

Mycosis can be classified into two types, that is, superficial mycosis represented by various trichophytosis, marginated eczema, psoriasis, cutaneous candidiasis or the like and deep seated mycosis represented by mycotic meningitis, mycotic infectious disease of respiratory organ, fungemia, mycosis of urinary tract or the like. Of these, deep seated mycosis such as candidiasis or aspergillosis tends to show a marked increase in recent days owing to the frequent use of an anticancer chemotherapeutic agent or immunosuppressive agent or lowering in the bioimmunology due to HIV infection or the like. There is accordingly a demand for a pharmaceutical efficacious against fungi causing such diseases. At present, pharmaceuticals effective against Aspergillus spp. and Candida spp. are not so many. As a remedy for such deep seated mycosis, Amphotericin B and azole base compounds such as Fluconazole and Itraconazole are conventionally known, but they involve problems in safety and antimycotic activity. There is accordingly a demand for an antimycotic agent effective against Aspergillus spp. and Candida spp. Now, more effective azole base compounds are under development. For example, as a compound having a hydroxyethyl group, compounds described in Japanese Patent Application Laid-Open No. 247944/1994 or the like and as a compound having a difluoromethylene group, those described in Japanese Patent Application Laid-Open No. 163374/1984, Japanese Patent Application Laid-Open No. 163269/1993 or the like are known but they are not fully satisfactory.

Accordingly, an object of the present invention is to provide a compound which has high safety and has antimycotic activity effective against Aspergillus spp. and Candida spp.

With the forgoing in view, the present inventors synthesized a number of triazole derivatives and salts thereof and carried out an investigation on their antimycotic activity effective against Aspergillus spp. and Candida spp. As a result, it has been found that a triazole derivative represented by the below-described formula (1) and a salt thereof have excellent antimycotic activity against fungi including Aspergillus spp. and Candida spp. and at the same time have high safety, leading to the completion of the present invention.

SUMMARY OF THE INVENTION

In one aspect of the present invention, there is thus provided a triazole derivative represented by the following formula (1):

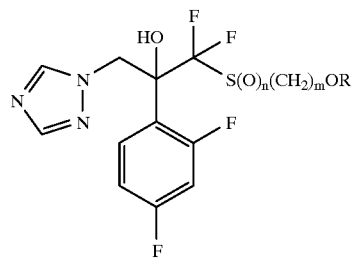

(1)

wherein R represents a hydrogen atom, an alkyl group, an aralkyl group or an acyl group, n stands for 0 to 2 and m stands for 1 to 5 or salt thereof, and an intermediate for the preparation of the derivative or salt.

In another aspect of the present invention, there is also provided a pharmaceutical comprising the triazole derivative (1) or salt thereof as an effective ingredient.

In a further aspect of the present invention, there is also provided a pharmaceutical composition comprising the triazole derivative (1) or salt thereof and a pharmacologically acceptable carrier.

In a still further aspect of the present invention, there is also provided the use of the triazole derivative (1) or salt thereof as a pharmaceutical.

In a still further aspect of the present invention, there is also provided a preventive and curative method of mycotic infectious diseases, which comprises administering to a patient an effective amount of the triazole derivative represented by the above formula (1) or salt thereof.

The triazole derivative or salt thereof according to the present invention has strong antimycotic action, and a mycocide comprising the derivative or salt as an effective ingredient is useful for the prevention and treatment of mycotic infectious diseases of mammary animals including human.

DETAILED DESCRIPTION OF THE PREFERRED EMBODIMENTS

In the triazole derivative (1) of the present invention, examples of the alkyl group represented by R include linear or branched $C_{1-10}$ alkyl groups. Specific examples include methyl, ethyl, n-propyl, isopropyl, n-butyl, tertbutyl, pentyl, hexyl, octyl and decyl. Among them, $C_{1-6}$ alkyl groups are more preferred, with a methyl group being particularly preferred.

Examples of the aralkyl group include $C_{7-11}$ aralkyl groups. Among them, phenyl-$C_{1-5}$-alkyl groups are more preferred and specific examples include benzyl and phenetyl.

Examples of the acyl group include $C_{2-10}$ acyl groups, $C_{2-10}$ alkanoyl groups such as acetyl, propanoyl and octanoyl and $C_{7-10}$ aroyl groups such as benzoyl. Among them, in the present invention, $C_{2-10}$ alkanoyl groups are more preferred, with an acetyl group being particularly preferred. In addition, n is preferably 0 or 2, while m is preferably 2 to 4, with 2 being particularly preferred.

No particular limitation is imposed on the salt of the triazole derivative (1) of the present invention insofar as it is a pharmacologically acceptable salt. Examples include hydrochlorides, nitrates, hydrobromides, p-toluenesulfonates, methanesulfonates, fumarates, succinates and lactates.

The triazole derivative (1) according to the present invention has optical activity based on the asymmetric carbon.

The present invention therefore embraces racemic modifications and optically active substances. The present invention also embraces hydrates of these compounds.

The triazole derivative (1) or salt thereof according to the present invention can be prepared, for example, in accordance with the reaction scheme described below:

alkyloxyalkylthio, aralkyloxyalkylthio or acyloxyalkylthio group into Compound (3). Compound (1a) is introduced into Compound (1b) by subjecting the former to hydrolysis or catalytic reduction. Compound (1a) or Compound (1b) so obtained is oxidized into Compound (1c) or Compound (1d),

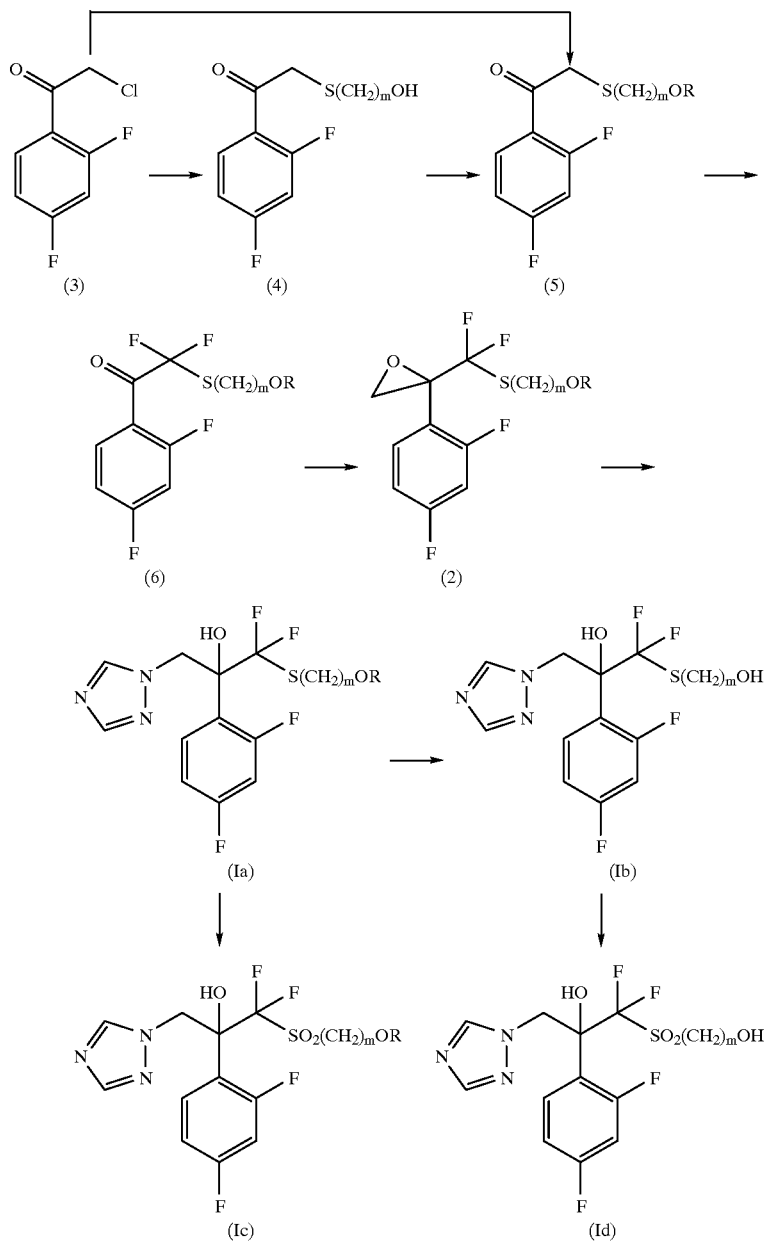

wherein R and m have the same meanings as defined above.

Described specifically, Compound (1a) can be prepared by introducing a hydroxyalkylthio group into 2-chloro-2', 4'-difluoroacetophenone (3), thereby forming Compound (4), subjecting the resulting Compound (4) to alkylation, aralkylation or acylation into Compound (5), fluorinating the resulting Compound (5) into Compound (6), epoxydizing the resulting Compound (6) into Compound (2), and then introducing a triazole group into Compound (2). Compound (5) is also available by directly introducing an respectively. Incidentally, Compound (2) is useful as an intermediate for the preparation of a triazole derivative (1).

Described more specifically, Compound (4) can be prepared by introducing a hydroxyalkylthio group into 2-chloro-2',4'-difluoroacetophenone (3) put on the market by Aldrich Chemical Co., Inc. As a hydroxyalkylthiolating reagent, ω-mercaptoalcohols such as 2-mercaptoethanol are usable. As a base, sodium hydroxide, potassium hydroxide, barium hydroxide, sodium carbonate, potassium carbonate, sodium hydride (NaH) or the like is usable. Examples of the solvent usable here include alcoholic solvents such as methanol and ethanol, nonaqueous polar solvents such as N,N-dimethylformamide (DMF) and etheric solvents such as 1,4-dioxane and tetrahydrofuran (THF), with methanol being preferred. The reaction temperature is −40° C. to the boiling point of the solvent, with 20 to 60° C. being preferred.

Compound (5) can be prepared by subjecting Compound (4) to alkylation, aralkylation or acylation in a solvent. Examples of the alkylating reagent usable here include alkyl halides such as methyl iodide and propyl iodide and sulfate esters such as dimethyl sulfate, those of the aralkylating reagent include aralkyl halides such as benzyl bromide and phenethyl chloride; and those of the acylating reagent include acyl halides such as acetyl chloride and propionic chloride and acid anhydrides such as acetic anhydride. As the solvent, it is possible to use a basic solvent such as pyridine singly or to use a hydrocarbon base solvent such as benzene or toluene or an etheric solvent such as diethyl ether or tetrahydrofuran in the presence of a base typified by potassium carbonate or sodium hydroxide. The reaction temperature is at −40° C. to the boiling point of the solvent, with 20 to 60° C. being preferred.

Compound (5) can also be prepared by introducing an alkyloxyalkylthio, aralkyloxyalkylthio or acyloxyalkylthio group directly to 2-chloro-2',4'-difluoroacetophenone (3). Compound (5) can be prepared, for example, by reacting 2-chloro-2',4'-difluoroacetophenone (3) with an alkyloxyalkylthiol such as 2-methyloxyethanethiol [J. Med. Chem., 39, 1253(1966).], an aralkyloxyalkylthiol such as benzyloxyethanethiol prepared similarly or an acyloxyalkyithiol such as 2-acetoxyethanethiol [J. Chem. Soc., 817(1952).] in the presence of a base such as sodium hydroxide, potassium hydroxide, barium hydroxide, sodium carbonate, potassium carbonate or sodium hydride in a solvent such as an alcoholic solvent, e.g., methanol or ethanol, a nonaqueous polar solvent, e.g., N,N-dimethylformamide or an etheric solvent such as 1,4-dioxane or tetrahydrofuran. Potassium carbonate and methanol can be given as the preferred examples of the base and solvent. The reaction temperature is −40° C. to the boiling point of the solvent, with 20 to 60° C. being preferred.

Compound (6) can be prepared by reacting Compound (5) with a fluorinating reagent in a solvent. Examples of the fluorinating reagent include fluorine gas, perchloryl fluoride, potassium fluoride, spray-dried potassium fluoride, freeze-dried potassium fluoride, tetraalkylammonium fluoride, tris(dimethylamino)sulfa(trimethylsilyl)difluoride, N-fluoropyridone, N-fluoro-N-alkyl-arenesulfonamide, N-fluoroquinuclidinium salt, N-fluoroperfluoroalkyl sulfonimide, N-fluorosaltum, fluorinated xenon, N-fluoropyridinium salt and N-fluoropyridinium sulfonate. Examples of the commercially available fluorinating reagent include "Onoda Fluorinates FP-T300, FP-T500, FP-T700, FP-B300, FP-B500, FP-B700 and FP-B800" (trade names; products of Chichibu Onoda Co., Ltd.) and "MEC-01, MEC-02, MEC-03, MEC-04 and MEC-05" (trade names; products of Daikin Industries, Ltd.). It is preferred to use the fluorinating reagent in an amount of 2 to 20 equivalents per mole of Compound (5). Illustrative of the solvent include 1,2-dichloroethane, 1,1,2-trichloroethane, chloroform, methylene chloride, diethyl ether, ethyl acetate and tetrahydrofuran. Among them, 1,1,2-trichloroethane can be used suitably. The reaction temperature is −78° C. to the boiling point of a solvent, with 80 to 100° C. being preferred. To improve the yield of the compound, a Lewis acid or a base can be used. Exemplary Lewis acids include aluminum chloride, zinc chloride and tin chloride, while exemplary bases include sodium hydroxide, potassium hydroxide, barium hydroxide, sodium carbonate, potassium carbonate, sodium hydride, potassium tert-butoxide, lithium diisopropylamide and potassium hexamethyldisilazane.

Compound (2) can be prepared by reacting Compound (6) with 1 to 2 equivalents of an epoxymethylating reagent such as trimethylsulfoxonium iodide or trimethylsulfonium iodide in the presence of 2 to 5 equivalents of an alkali. As the solvent, dimethylsulfoxide (DMSO), tetrahydrofuran or the like can be used suitably. Examples of the base include sodium hydroxide, potassium hydroxide, barium hydroxide, sodium carbonate, potassium carbonate, sodium hydride and sodium methoxide, with sodium hydride being particularly preferred. The reaction temperature is −100° C. to the boiling point of the solvent, with −40 to 50° C. being preferred.

Compound (1a) can be prepared by reacting Compound (2) with 1,2,4-triazole or an alkali metal salt thereof in a solvent in the presence of a base. As the solvent, N,N-dimethylformamide, acetonitrile, N,N-dimethylacetamide or dimethylsulfoxide can be used suitably. Examples of the base usable here include sodium hydroxide, potassium hydroxide, barium hydroxide, sodium carbonate, potassium carbonate or potassium tert-butoxide. The reaction temperature is 0° C. to the boiling point of the solvent, with 20 to 60° C. being preferred.

Compound (1b) can be prepared by hydrolyzing Compound (1a) in the presence of an acid or alkali. Examples of the acid usable here include hydrochloric acid, sulfuric acid and acetic acid, while those of the base include sodium hydroxide, potassium hydroxide and lithium hydroxide. Preferred examples of the solvent include alcoholic solvents such as methanol and ethanol. The reaction temperature is −40° C. to the boiling point of the solvent, with 20 to 60° C. being preferred.

Compound (1b) can also be prepared by subjecting Compound (1a) to catalytic reduction in the presence of a metal catalyst in a hydrogen gas. Examples of the metal catalyst include platinum, palladium, nickel, copper, ruthenium, alloys of these metals, and palladium-carbon. Examples of the solvent include alcoholic solvents such as methanol and ethanol and hydrocarbon base solvents such as benzene and toluene. It is preferred that the reaction temperature is 0° C. to the boiling point of the solvent and the pressure is 1 to 10 atmospheric pressure.

Compound (1c) can be prepared by reacting Compound (1a) with at least 2 equivalents, preferably 2.2 to 3 equivalents of an oxidizing agent. Examples of the oxidizing agent include m-chloroperbenzoic acid (mCPBA), aqueous hydrogen peroxide, peracetic acid, tetrapropylammonium perruthenate, osmium tetraoxide, potassium permanganate, oxone and sodium periodate. Illustrative of the usable solvent include chloroform, dichloromethane, acetic acid, methanol, water, acetonitrile and carbon tetrachloride, and mixtures thereof. The reaction temperature is −40° C. to the boiling point of the solvent, with 0 to 50° C. being preferred. To improve the yield, ruthenium trichloride, selenium dioxide, sodium tungstate, sodium molybdate and vanadium oxide can be used as a catalyst.

Compound (1d) can be prepared by reacting Compound (1b) with at least 2 equivalents, preferably 2.2 to 3 equivalents of an oxidizing agent. Examples of the oxidizing agent include m-chloroperbenzoic acid (mCPBA), aqueous hydrogen peroxide, peracetic acid, tetrapropylammonium perruthenate, osmium tetraoxide, potassium permanganate, oxone and sodium periodate. Illustrative of the usable solvent include chloroform, dichloromethane, acetic acid, methanol, water, acetonitrile and carbon tetrachloride, and mixtures thereof. The reaction temperature is −40° C. to the boiling point of the solvent, with 0 to 50° C. being preferred. To improve the yield, ruthenium trichloride, selenium dioxide, sodium tungstate, sodium molybdate, vanadium oxide or the like can be used as a catalyst, with sodium tungstate being preferred.

No particular limitation is imposed on the isolation means of a target product from the reaction mixture available by each of the above-described reactions. The target product can be isolated, for example, by recrystallization, various types of chromatography or the like. Moreover, the target compound can be converted into a desired salt in a manner known per se in the art.

The invention Compound (1) or salt thereof so obtained has excellent in vivo or in vitro antimycotic action against fungi including Aspergillus spp. and Candida spp. and at the same time has high safety so that it is useful as a pharmaceutical for the prevention and treatment of various mycotic infectious diseases.

The invention compound can be prepared as a pharmaceutical composition in various dosage forms such as tablets, granules, powders, capsules, suspensions, injections, suppositories and external preparations in a conventional manner by adding thereto a pharmacologically acceptable carrier as needed. It is preferred for the preparation of a solid preparation that after an excipient and optionally a binder, disintegrator, extender, coating agent, sugarcoating agent and/or the like is added to the invention compound, the resulting mixture is formed into tablets, granules, capsules, suppositories or the like in a manner known per se in the art. For the preparation of an injection, it is only necessary to dissolve, disperse or emulsify the invention compound in an aqueous carrier such as distilled water for injection in advance or to prepare powder for injection and dissolve it upon use. Examples of the administration method of the injection include intravenous administration, intraarterial administration, intraperitoneal administration, subcutaneous administration and instillation.

The administration amount of the invention compound differs depending on the administration method, symptoms, weight and age of the patient to be administered but administration of 0.1 to 100 mg/day per adult is preferred.

EXAMPLES

The present invention will hereinafter be described in detail by Examples. It should however be borne in mind that the present invention will not be limited to or by the following examples.

Referential Example 1
Synthesis of 2-ethoxyethanethiol

A solution of 1-chloro-2-ethoxyethane (10.0 g, 0.092 mol) and thiourea (7.0 g; 0.092 mol) in 95% ethanol (50 ml) was refluxed for 24 hours. To the reaction mixture, sodium hydroxide (5.3 g, 0.132 mol) and water (53 ml) were added and they were refluxed for 5 hours. The solvent was then distilled off under reduced pressure. The residue was neutralized with a 10% aqueous solution of sulfuric acid, followed by extraction with ethyl ether. The ether solution was washed with water, dried over sodium sulfate and then distilled off under reduced pressure, whereby 2-ethoxyethanethiol (4.8 g, yield: 49.0%) was obtained as a colorless oil.

$^1$H-NMR (CDCl$_3$)δ: 1.20(3H,t,J=7.0 Hz), 1.58(1H,t,J=8.4 Hz), 2.5–3.0(2H,m), 3.3–3.8(4H,m).

Referential Example 2
Synthesis of 2-benzyloxyethanethiol

A solution of 2-benzyloxy-1-chloroethane (Synthesis, 1990, 495.) (7.2 g, 0.043 mol) and thiourea (3.2 g; 0.043 mol) in 95% ethanol (50 ml) was refluxed for 24 hours. To the reaction mixture, potassium hydroxide (4 g, 0.061 mol) and water (40 ml) were added and they were refluxed for 5 hours. The solvent was then distilled off under reduced pressure. The residue was neutralized with a 10% aqueous solution of sulfuric acid, followed by extraction with ethyl ether. The ether solution was washed with water, dried over sodium sulfate and then distilled off under reduced pressure, whereby 2-benzyloxyethanethiol (4.2 g, yield: 59.0%) was obtained as a colorless oil.

$^1$H-NMR (CDCl$_3$)δ: 1.58(1H,t,J=7.9 Hz), 2.5–3.0(2H,m), 3.60(2H,t,J=6.4 Hz), 4.53(2H,s), 7.33(5H,s).

Example 1
Synthesis of 2',4'-difluoro-2-(2-hydroxyethyl)thioacetophenone

To a solution of 2-chloro-2',4'-difluoroacetophenone (159 g, 0.8 mol) and 2-mercaptoethanol (77.9 g, 1.0 mol) in methanol (1000 ml), potassium carbonate (138 g, 1.0 mol) was added under ice cooling, followed by stirring at room temperature for 0.5 hour. After the completion of the reaction, an insoluble matter was filtered off. The filtrate was then distilled off under reduced pressure. The residue so obtained was diluted with ethyl ether, washed with water and dried over magnesium sulfate. The solvent was distilled off under reduced pressure, whereby 2',4'-difluoro-2-(2-hydroxyethyl)thioacetophenone (190 g, yield: 98%) was obtained as a colorless oil.

$^1$H-NMR (CDCl$_3$)δ: 2.72(2H,t,J=6.2 Hz), 3.5–4.0(4H,m), 3.7(1H,br.s), 6.7–7.2(2H,m), 7.7–8.2(1H,m).

Example 2
Synthesis of 2-(2-acetoxyethyl)thio-2',4'-difluoroacetophenone (1) To a solution of 2',4'-difluoro-2-(2-hydroxyethyl)thioacetophenone (190 g, 0.8 mol) in pyridine (1000 ml), acetic anhydride (150 g, 1.5 mol) was added, followed by stirring at an external temperature of 60° C. for 1.5 hours. After the completion of the reaction, the reaction mixture was distilled off under reduced pressure and the residue was extracted with ethyl ether. The ether solution was washed with a saturated aqueous solution of copper sulfate and water, dried over magnesium sulfate and distilled off under reduced pressure. The residue so obtained was purified by chromatography on a silica gel column, whereby from the fraction eluted with chloroform, 2-(2-acetoxyethyl)thio-2',4'-difluoroacetophenone (176 g, yield: 78.7%) was obtained as a pale yellow oil.

(2) Using 2-chloro-2',4'-difluoroacetophenone (2.0 g, 0.010 mol), 2-acetoxyethanethiol (J. Chem. Soc., 1952, 817.) (1.5 g, 0.013 mol), potassium carbonate (1.8 g, 0.013 mol) and methanol (50 mol), 2-(2-acetoxyethyl)thio-2',4'-difluoroacetophenone (1.8 g, yield: 62.0%) was obtained as a colorless oil by similar procedures to Example 1.

$^1$H-NMR (CDCl$_3$)δ: 2.06(3H,s), 2.76(2H,t,J=6.4 Hz), 3.83(2H,d,J=2.4 Hz), 4.23(2H,t,J=6.4 Hz), 6.7–7.1(2H,m), 7.8–8.2(1H,m)

Example 3
Synthesis of 2',4'-difluoro-2-(2-methoxyethyl)thioacetophenone

Using 2-chloro-2',4'-difluoroacetophenone (2.7 g, 0.014 mol), 2-methoxyethanethiol [J. Med. Chem., 39, 1253(1996).] (1.4 g, 0.015 mol), potassium carbonate (2.3 g, 0.016 mol) and methanol (50 ml), 2',4'-difluoro-2-(2-methoxyethyl)thioacetophenone (2.3 g, yield: 67.0%) was obtained as a colorless oil by similar procedures to Example 1.

$^1$H-NMR (CDCl$_3$)δ: 2.71(2H,t,J=6.4 Hz), 3.38(3H,s), 3.56(2H,t,J=6.4 Hz), 3.84(2H,d,J=2.4 Hz), 6.7–7.1(2H,m), 7.7–8.1(1H,m).

Example 4

Synthesis of 2-(2-ethoxyethyl)thio-2',4'-difluoroacetophenone

Using 2-chloro-2',4'-difluoroacetophonone (7.8 g, 0.041 mol), 2-ethoxyethanethiol (4.8 g 0.045 mol), potassium carbonate (6.2 g, 0.045 mol) and methanol (50 ml), 2-(2-ethoxyethyl)thio-2',4'-dilfuoroacetophenone (5.4 g, yield: 50.0%) was obtained as a colorless oil by similar procedures to Example 1.

$^1$H-NMR (CDCl$_3$)δ: 1.17(3H,t,J=7.0 Hz), 2.71(2H,t,J=6.4 Hz), 3.2–3.7(4H,m), 3.85(2H,d,J=2.4 Hz), 6.7–7.1(2H,m), 7.7–8.1(1H,m).

Example 5

Synthesis of 2-(2-benzyloxyethyl)thio-2',4'-difluoroacetophenone

Using 2-chloro-2',4'-difluoroacetophenone (4.5 g, 0.024 mol), 2-benzyloxyethanethiol (4.2 g, 0.025 mol), potassium carbonate (4.0 g, 0.029 mol) and methanol (50 ml), 2-(2-benzyloxyethyl)thio-2',4'-difluoroacetophenone (6.2 g, yield: 80.8%) was obtained as a colorless oil by similar procedures to Example 1.

$^1$H-NMR (CDCl$_3$)δ: 2.74(2H,t,J=6.4 Hz), 3.64(2H,t,J=6.4 Hz), 3.83(2H,d,J=2.4 Hz), 4.51(2H,s), 6.7–7.1(2H,m), 7.30 (5H,s), 7.7–8.1(1H,m).

Example 6

Synthesis of 2-(2-acetoxyethyl)thio-2,2-difluoro-2',4'-difluoroacetophenone

To a solution of 2-(2-acetoxyethyl)thio-2',4'-difluoroacetophenone (90.0 g, 0.3 mol) in 1,1,2-trichloroethane (1500 ml), N-fluoropyridinium triflate ("Onoda Fluorinate FP-T500") (211 g, 0.9 mol) was added in portions, followed by stirring at an internal temperature of 100 to 110° C. for 2.5 hours. After the completion of the reaction, the reaction mixture was diluted with ethyl ether and an insoluble matter was filtered off. The ether solution was washed with water, dried over magnesium sulfate and then distilled off under reduced pressure. The residue so obtained was subjected to chromatography on a silica gel column, whereby from the fraction eluted with chloroform, 2-(2-acetoxyethyl)thio-2,2-difluoro-2',4'-difluoroacetophenone (25.5 g, yield: 26.6%) was obtained as a colorless oil.

$^1$H-NMR (CDCl$_3$)δ: 2.07(3H,s), 3.14(2H,t,J=6.6 Hz), 4.31(2H,t,J=6.6 Hz), 6.8–7.2(2H,m), 7.8–8.2(1H,m).

Example 7

Synthesis of 2,2-difluoro-2',4'-difluoro-2-(2-methoxyethyl)thioacetophenone

To a solution of 2',4'-difluoro-2-(2-methoxyethyl)thioacetophenone (1.00 g, 0.004 mol) in 1,1,2-trichloroethane (50 ml), N-fluoro-4-methylpyridinium-2-sulfonate ("MEC-02", trade name; product of Daikin Industries, Ltd.) (2.17 g, 0.011 mol) was added in portions at an internal temperature of 85° C., followed by stirring at an internal temperature of 100 to 110° C. for 2 hours. After the completion of the reaction, the reaction mixture was diluted with ethyl ether and an insoluble matter was filtered off. The ether solution was washed with water, dried over magnesium sulfate and distilled off under reduced pressure. The residue so obtained was subjected to chromatography on a silica gel column, whereby from the fraction eluted with chloroform, 2,2-difluoro-2',4'-difluoro-2-(2-methoxy-ethyl) thioacetophenone (0.43 g, yield: 39.0%) was obtained as a pale yellow oil.

$^1$H-NMR (CDCl$_3$)δ: 3.08(2H,t,J=6.2 Hz), 3.46(3H,s), 3.64(2H,t,J=6.2 Hz), 6.7–7.1(2H,m), 7.7–8.1(1H,m).

Example 8

Synthesis of 2-(2-ethoxyethyl)thio-2,2-difluoro-2',4'-difluoroacetophenone

Using 2-(2-ethoxyethyl)thio-2',4'-difluoroacetophenone (5.4 g, 0.021 mol), 1,1,2-trichloroethane (100 ml) and N-fluoro-4-methylpyridinium-2-sulfonate ("MEC-02", product of Daikin Industries, Ltd.) (11.1 g, 0.058 mol), 2-(2-ethoxyethyl)thio-2,2-difluoro-2',4'-difluoroacetophenone (3.1 g, yield: 39%) was obtained as a pale yellow oil by similar procedures to Example 7.

$^1$H-NMR (CDCl$_3$)δ: 1.27(3H,t,J=7.0 Hz), 3.08(2H,t,J=6.6 Hz), 3.3–3.8(4H,m), 6.7–7.1(2H,m), 7.7–8.1(1H,m).

Example 9

Synthesis of 2-(2-benzyloxyethyl)thio-2,2-difluoro-2',4'-difluoroacetophenone

Using 2-(2-benzyloxyethyl)thio-2',4'-difluoroacetophenone (5.4 g, 0.017 mol), 1,1,2-trichloroethane (100 ml) and N-fluoro-4-methylpyridinium-2-sulfonate ("MEC-02", product of Daikin Industries, Ltd.) (9.0 g, 0.047 mol), 2-(2-benzyloxyethyl)thio-2,2-difluoro-2',4'-difluoroacetophenone (3.0 g, yield: 50%) was obtained as a pale yellow oil by similar procedures to Example 7.

$^1$H-NMR (CDCl$_3$)δ: 3.11(2H,t,J=5.9 Hz), 3.73(2H,t,J=5.9 Hz), 4.54(2H,s), 6.7–7.1(2H,m), 7.32(5H,s), 7.7–8.1(1H,m).

Example 10

Synthesis of 1-(2-acetoxyethyl)thio-2-(2,4-difluorophenyl)-1,1-difluoro-2,3-epoxypropane A suspension of 60% NaH (3.95 g, 0.1 mol) in THF (60 ml)-DMSO (120 ml) was heated to an external temperature of 50° C., followed by the addition of trimethylsulfoxonium iodide (21.7 g, 0.1 mol) in portions. The resulting mixture was stirred for 15 minutes at the same temperature and was then cooled to −20° C. To the reaction mixture, a solution of 2-(2-acetoxyethyl)thio-2,2-difluoro-2',4'-difluoroacetophenone (25.5 g, 0.08 mol) in THF (60 ml) was added dropwise. After being stirred at room temperature for 1.5 hours, the reaction mixture was poured into ice water, followed by extraction with ethyl ether. The ether solution was washed with water, dried over magnesium sulfate and then distilled off under reduced pressure, whereby 1-(2-acetoxyethyl)thio-2-(2,4-difluorophenyl)-1,1-difluoro-2,3-epoxypropane (24.0 g, yield: 90.0%) was obtained as a pale yellow oil.

$^1$H-NMR (CDCl$_3$)δ: 2.05(3H,s), 2.8–3.2(3H,m), 3.5–3.6 (1H,m), 4.24(2H,t,J=6.6 Hz), 6.7–7.1(2H,m), 7.3–7.7(1H, m).

Example 11

Synthesis of 2-(2,4-difluorophenyl)-1,1-difluoro-1-(2-methoxyethyl)thio-2,3-epoxypropane Using 60% NaH (2.2 g, 0.055 mol), THF (60 ml)-DMSO (120 ml), trimethylsulfoxonium iodide (12.1 g, 0.055 mol) and a solution of 2,2-difluoro-2',4'-difluoro-2-(2-methoxyethyl)thioacetophenone (13.0 g, 0.046 mol) in THF (60 ml), 2-(2,4-difluorophenyl)-1,1-difluoro-1-(2-methoxy-ethyl)thio-2,3-epoxypropane (13.0 g, yield: 95.4%) was obtained as a pale yellow oil by similar procedures to Example 10.

¹H-NMR (CDCl₃)δ: 2.6–2.8(1H,m), 3.01(2H,t,J=6.4 Hz), 3.35(3H,s), 3.4–3.7(3H,m), 6.6–7.1(2H,m), 7.4–7.7(1H,m).

Example 12
Synthesis of 2-(2,4-difluorophenyl)-1-(2-ethoxyethyl)thio-1,1-difluoro-2,3-epoxypropane Using 60% NaH (0.5 g, 0.013 mol), THF (15 ml)-DMSO (30 ml), trimethylsulfoxonium iodide (2.8 g, 0.013 mol) and a solution of 2-(2-ethoxyethyl)thio-2,2-difluoro-2',4'-difluoroacetophenone (3.1 g, 0.01 mol) in THF (15 ml), 2-(2,4-difluorophenyl)-1-(2-ethoxyethyl)thio-1,1-difluoro-2,3-epoxypropane (3.1 g, yield: 96.0%) was obtained as a pale yellow oil by similar procedures to Example 10.

¹H-NMR (CDCl₃)δ: 1.0–1.4(3H,m), 2.8–3.1(3H,m), 3.3–4.2(5H,m), 6.6–7.1(2H,m), 7.3–7.7(1H,m).

Example 13
Synthesis of 1-(2-benzyloxyethyl)thio-2-(2,4-difluorophenyl)-1,1-difluoro-2,3-epoxypropane Using 60% NaH (0.4 g, 0.010 mol), THF (15 ml)-DMSO (30 ml), trimethylsulfoxonium iodide (2.2 g, 0.01 mol) and a solution of 2-(2-benzyloxyethyl)thio-2,2-difluoro-2',4'-difluoroacetophenone (3.0 g, 0.008 mol) in THF (15 ml), 1-(2-benzyloxyethyl)thio-2-(2,4-difluorophenyl)-1,1-difluoro-2,3-epoxypropane (3.0 g, yield: 96.0%) was obtained as a pale yellow oil by similar procedures to Example 10.

¹H-NMR (CDCl₃)δ: 2.6–3.2(3H,m), 3.4–3.8(3H,m), 4.51(2H,s), 6.6–7.0(2H,m), 7.31(5H,s), 7.3–7.7(1H,m).

Example 14
Synthesis of 1-(2-acetoxyethyl)thio-2-(2,4-difluorophenyl)-1,1-difluoro-3-(1H-1,2,4-triazol-1-yl)propan-2-ol To a solution of 1-(2-acetoxyethyl)thio-2-(2,4-difluorophenyl)-1,1-difluoro-2,3-epoxypropane (24.0 g, 0.07 mol) in DMF (250 ml), 1,2,4-triazole (16.6 g, 0.24 mol) and potassium carbonate (33.2 g, 0.24 mol) were added, followed by stirring at room temperature for 12 hours and then at an external temperature of 50° C. for one hour. After the completion of the reaction, the reaction mixture was diluted with ethyl ether and an insoluble matter was filtered off. The ether solution was washed with water, dried over magnesium sulfate and then distilled off under reduced pressure. The residue so obtained was recrystallized from isopropyl ether-ethyl acetate, whereby 1-(2-acetoxyethyl)thio-2-(2,4-difluorophenyl)-1,1-difluoro-3-(1H-1,2,4-triazol-1-yl)propan-2-ol (12.2 g, yield: 37.8%) was obtained as colorless crystals.

Melting point: 79 to 82° C.; IR(KBr) $v_{max}$cm⁻¹: 1731, 1145; MS (FAB): 394 (M+H) ¹H-NMR (CDCl₃)δ: 2.05(3H, s), 3.05(2H,t,J=6.6 Hz), 4.24(2H,t,J=6.6 Hz), 4.80(1H,d,J=14.3 Hz), 5.30(1H,d,J=14.3 Hz), 5.83(1H,s), 6.6–7.0(2H,m), 7.6–7.9(1H,m), 7.81(1H,s), 8.08(1H,s)

Example 15
Synthesis of 2-(2,4-difluorophenyl)-1,1-difluoro-1-(2-methoxyethyl)thio-3-(1H-1,2,4-triazol-1-yl)propan-2-ol Using 2-(2,4-difluorophenyl)-1,1-difluoro-1-(2-methoxyethyl)thio-2,3-epoxypropane (13.0 g, 0.044 mol), DMSO (100 ml), 1,2,4-triazole (7.6 g, 0.11 mol) and potassium carbonate (15.2 g, 0.11 mol), 2-(2,4-difluorophenyl)-1,1-difluoro-1-(2-methoxyethyl)thio-3-(1H-1,2,4-triazol-1-yl)propan-2-ol (2.0 g, yield: 12.0%) was obtained as colorless crystals by similar procedures to Example 14.

Melting point: 80 to 81° C.; IR(KBr) $v_{max}$cm⁻¹: 1130; MS (FAB): 366 (M+H) ¹H-NMR (CDCl₃)δ: 3.01(2H,t,J=6.6 Hz), 3.35(3H,s), 3.58(2H,t,J=6.6 Hz), 4.81(1H,d,J=14.5 Hz), 5.29(1H,d,J=14.5 Hz), 5.80(1H,s), 6.5–6.9(2H,m), 7.6–7.9(1H,m), 7.80(1H,s), 8.09(1H,s).

Example 16
Synthesis of 2-(2,4-difluorophenyl)-1-(2-ethoxyethyl)thio-1,1-difluoro-3-(1H-1,2,4-triazol-1-yl)propan-2-ol Using 2-(2,4-difluorophenyl)-1-(2-ethyoxyethyl)thio-1,1-difluoro-2,3-epoxypropane (3.1 g, 0.01 mol), DMSO (30 ml), 1,2,4-triazole (1.7 g, 0.025 mol) and potassium carbonate (3.4 g, 0.025 mol), 2-(2,4-difluorophenyl)-1-(2-ethoxyethyl)thio-1,1-difluoro-3-(1H-1,2,4-triazol-1-yl)propan-2-ol (1.0 g, yield: 25.0%) was obtained as colorless crystals by similar procedures to Example 14.

Melting point: 61 to 63° C.; IR(KBr) $v_{max}$cm⁻¹: 1132; MS (FAB): 380 (M+H); ¹H-NMR (CDCl₃)δ: 1.19(3H,t,J=6.8 Hz), 3.01(2H,t,J=6.4 Hz), 3.3–3.8(4H,m), 4.80(1H,d,J=14.3 Hz), 5.29(1H,d,J=14.3 Hz), 5.70(1H,s), 6.6–7.0(2H,m), 7.6–7.9(1H,m), 7.81(1H,s), 8.08(1H,s).

Example 17
Synthesis of 1-(2-benzyloxyethyl)thio-2-(2,4-difluorophenyl)-1,1-difluoro-3-(1H-1,2,4-triazol-1-yl)propan-2-ol Using 1-(2-benzyloxyethyl)thio-2-(2,4-difluorophenyl)-1,1-difluoro-2,3-epoxypropane (3.0 g, 0.008 mol), DMSO (30 ml), 1,2,4-triazole (1.4 g, 0.02 mol) and potassium carbonate (2.8 g, 0.02 mol), 1-(2-benzyloxyethyl)thio-2-(2,4-difluorophenyl)-1,1-difluoro-3-(1H-1,2,4-triazol-1-yl)propan-2-ol (0.62 g, yield: 17.4%) was obtained as a colorless oil by similar procedures to Example 14.

IR(CHCl₃) $v_{max}$cm⁻¹: 1140; MS (FAB): 442 (M+H); ¹H-NMR (CDCl₃)δ: 3.04(2H,t,J=6.4 Hz), 3.67(2H,t,J=6.4 Hz), 4.52(2H,s), 4.79(1H,d,J=14.7 Hz), 5.27(1H,d,J=14.7 Hz), 5.72(1H,s), 6.5–7.0(2H,m), 7.31(5H,s), 7.5–7.9(1H,m), 7.80(1H,s), 8.06(1H,s).

Example 18
Synthesis of 2-(2,4-difluorophenyl)-1,1-difluoro-1-(2-hydroxyethyl)thio-3-(1H-1,2,4-triazol-1-yl)propan-2-ol (1) To a solution of 1-(2-acetoxyethyl)thio-2-(2,4-difluorophenyl)-1,1-difluoro-3-(1H-1,2,4-triazol-1-yl)propan-2-ol (14.3 g, 0.12 mol) in ethanol (200 ml), a 10% aqueous solution (20 ml) of lithium hydroxide monohydrate was added and they were stirred at room temperature for one hour. After the completion of the reaction, the reaction mixture was distilled off under reduced pressure. Water was added to the residue so obtained, followed by extraction with chloroform. The chloroform solution was washed with water, dried over magnesium sulfate and then distilled off under reduced pressure, whereby 2-(2,4-difluorphenyl)-1,1-difluoro-1-(2-hydroxyethyl)thio-3-(1H-1,2,4-triazol-1-yl)propan-2-ol (11.4 g, yield: 89.8%) was obtained as colorless crystals.

(2) To a solution of 1-(2-benzyloxyethyl)thio-2-(2,4-difluorophenyl)-1,1-difluoro-3-(1H-1,2,4-triazol-1-yl)propan-2-ol (1.0 g, 2.2 mmol) in ethanol (20 ml), palladium black (20 mg, catalytic) was added, followed by stirring at room temperature and 1 atmospheric pressure in a hydrogen gas for 12 hours. After the completion of the reaction, an insoluble matter was filtered off. The solvent was then distilled off under reduced pressure. To the residue so obtained, water was added, followed by extraction with chloroform. The chloroform solution was washed with water, dried over magnesium sulfate and then distilled off under reduced pressure. To the residue, isopropyl ether was added for crystallization, whereby 2-(2,4-difluorphenyl)-1,1-difluoro-1-(2-hydroxyethyl)thio-3-(1H-1,2,4-triazol-1-yl)propan-2-ol (0.46 g, yield: 55.0%) was obtained as colorless crystals.

Melting point: 87 to 90° C.; IR(KBr) $v_{max}$cm⁻¹: 1504, 1146; MS (FAB): 352 (M+H); ¹H-NMR (CDCl₃)δ: 2.99(2H, t,J=5.9 Hz), 3.21(1H,br.s), 3.6–4.0(2H,m), 4.81(1H,d,J=14.5 Hz), 5.28(1H,d,J=14.5 Hz), 6.16(1H,d,J=2.2 Hz), 6.6–7.0 (2H,m), 7.5–7.9(1H,m), 7.77(1H,s), 8.11(1H,s).

Example 19
Synthesis of 1-(2-acetoxyethyl)sulfonyl-2-(2,4-difluorophenyl)-1,1-difluoro-3-(1H-1,2,4-triazol-1-yl)propan-2-ol To a solution of 1-(2-acetoxyethyl)thio-2-(2,4-difluorophenyl)-1,1-difluoro-3-(1H-1,2,4-triazol-1-yl)propan-2-ol (0.39 g, 1.0 mmol) in carbon tetrachloride (2 ml)—acetonitrile (2 ml), a solution of ruthenium trichloride (0.01 g, 0.05 mmol) and sodium periodate (0.64 g, 3.0 mmol) in water (4 ml) was added, followed by stirring for 12 hours. After the completion of the reaction, the reaction mixture was diluted with chloroform and an insoluble matter was filtered off. After the filtrate was washed with water and dried, the solvent was distilled off under reduced pressure. The residue so obtained was subjected to chromatography on a silica gel column, whereby from the fraction eluted with chloroform, 1-(2-acetoxyethyl)sulfonyl-2-(2,4-difluorophenyl)-1,1-difluoro-3-(1H-1,2,4-triazol-1-yl)propan-2-ol (0.06 g, yield: 14.1%) was obtained as colorless crystals.

Melting point: 77 to 80° C.; IR(KBr) $v_{max}$cm$^{-1}$: 1740, 1346, 1154, 1115; MS (FAB): 426 (M+H); $^1$H-NMR (CDCl$_3$)δ: 2.05(3H,s), 3.75(2H,t,J=6.6 Hz), 4.62(2H,t,J=6.6 Hz), 5.15(1H,d,J=15 Hz), 5.40(1H,d,J=15 Hz), 6.40(1H, br.s), 6.6–7.0(2H,m), 7.4–7.9(1H,m), 7.83(1H,s), 8.17(1H, s).

Example 20
Synthesis of 2-(2,4-difluorophenyl)-1,1-difluoro-1-(2-hydroxyethyl)sulfonyl-3-(1H-1,2,4-triazol-1-yl)propan-2-ol To a solution of 2-(2,4-difluorophenyl)-1,1-difluoro-1-(2-hydroxyethyl)thio-3-(1H-1,2,4-triazol-1-yl)propan-2-ol (9.10 g, 0.026 mol) in dichloromethane (250 ml), 85% m-chloroperbenzoic acid (14.8 g, 0.073 mol) was added at room temperature, followed by stirring at room temperature for one hour. After the completion of the reaction, a saturated aqueous solution of sodium thiosulfate and a saturated solution of sodium bicarbonate were added to the reaction mixture and they were stirred. The dichloromethane solution was separated, washed with water, dried over anhydrous magnesium sulfate and then distilled off under reduced pressure. The residue so obtained was recrystallized from isopropyl ether—ethyl acetate, whereby 2-(2,4-difluorophenyl)-1,1-difluoro-1-(2-hydroxyethyl)sulfonyl-3-(1H-1,2,4-triazol-1-yl)propan-2-ol (4.43 g, yield: 44.6%) was obtained as colorless crystals.

Melting point: 113 to 115° C.; IR(KBr) $v_{max}$cm$^{-1}$: 1327, 1148, 1118; MS (FAB): 384 (M+H); $^1$H-NMR (CDCl$_3$)δ: 2.56(1H,t,J=6.6 Hz), 3.5–3.8(2H,m), 4.1–4.4(2H,m), 5.15 (1H,d,J=15.0 Hz), 5.37(1H,d,J=15.0 Hz), 6.14(1H,d,J=2.2 Hz), 6.6–7.0(2H,m), 7.5–7.9(1H,m), 7.81(1H,s), 8.06(1H,s).

Example 21
Synthesis of 2-(2,4-difluorophenyl)-1,1-difluoro-1-(2-methoxyethyl)sulfonyl-3-(1H-1,2,4-triazol-1-yl)propan-2-ol Using 2-(2,4-difluorophenyl)-1,1-difluoro-1-(2-methoxyethyl)thio-3-(1H-1,2,4-triazol-1-yl)propan-2-ol (4.0 g, 0.011 mol), dichloromethane (100 ml) and 70% m-chlorobenzoic acid (6.5 g, 0.026 mol), 2-(2,4-difluorophenyl)-1,1-difluoro-1-(2-methoxyethyl)sulfonyl-3-(1H-1,2,4-triazol-1-yl)propan-2-ol (2.0 g, yield: 47.0%) was obtained as colorless crystals by similar procedures to Example 20.

Melting point: 93 to 91° C.; IR(KBr) $v_{max}$cm$^{-1}$: 1331, 1148, 1118; MS (FAB): 398 (M+H); $^1$H-NMR (CDCl$_3$)δ: 3.42(3H,s), 3.5–3.7(2H,m), 3.7–4.0(2H,m), 5.16(1H,d,J= 15.4 Hz), 5.37(1H,d,J=15.4 Hz), 6.17(1H,d,J=1.8 Hz), 6.6–7.0(2H,m), 7.5–7.8(1H,m), 7.77(1H,s), 8.06(1H,s).

Example 22
Synthesis of 2-(2,4-difluoropheyl)-1-(2-ethoxyethyl)-sulfonyl-1,1-difluoro-3-(1H-1,2,4-triazol-1-yl)propan-2-ol Using 2-(2,4-difluorophenyl)-1-(2-ethoxyethyl)thio-1,1-difluoro-3-(1H-1,2,4-triazol-1-yl)propan-2-ol (0.68 g, 1.80 mmol), dichloromethane (30 ml) and 70% m-chloroperbenzoic acid (1.07 g, 4.33 mmol), 2-(2,4-difluorophenyl)-1-(2-ethoxyethyl)sulfonyl-1,1-difluoro-3-(1H-1,2,4-triazol-1-yl)propan-2-ol (0.52 g, yield: 71.0%) was obtained as colorless crystals by similar procedures to Example 20.

Melting point: 89 to 91° C.; IR(KBr) $v_{max}$cm$^{-1}$: 1331, 1156, 1118; MS (FAB): 412 (M+H); $^1$H-NMR (CDCl$_3$)δ: 1.21(3H,t,J=6.7 Hz), 3.4–3.8(4H,m), 3.8–4.1(2H,m), 5.15 (1H,d,J=16.0 Hz), 5.38(1H,d,J=16.0 Hz), 6.04(1H,br.s), 6.6–7.0(2H,m), 7.5–7.8(1H,m), 7.80(1H,s), 8.05(1H,s).

Example 23
Synthesis of 1-(2-benzyloxyethyl)sulfonyl-2-(2,4-difluorophenyl)-1,1-difluoro-3-(1H-1,2,4-triazol-1-yl)propan-2-ol Using 1-(2-benzyloxyethyl)thio-2-(2,4-difluorophenyl)-1,1-difluoro-3-(1H-1,2,4-triazol-1-yl)propan-2-ol (1.0 g, 2.27 mmol), dichloromethane (50 ml) and 70% m-chlorobenzoic acid (1.7 g, 6.8 mol), 1-(2-benzyoxyethyl)-sulfonyl-2-(2,4-difluorophenyl)-1,1-difluoro-3-(1H-1,2,4-triazol-1-yl)propan-2-ol (0.23 g, yield: 21.5%) was obtained as colorless oil by similar procedures to Example 20.

IR (CHCl$_3$) $v_{max}$cm$^{-1}$: 1337, 1141, 1120; MS (FAB): 474 (M+H); $^1$H-NMR (CDCl$_3$)δ: 3.69(2H,t,J=5.7 Hz), 4.01(2H, t,J=5.7 Hz), 4.59(2H,s), 5.14(1H,d,J=14.9 Hz), 5.35(1H,d, J=14.9 Hz), 6.09(1H,d,J=2.6 Hz), 6.6–7.0(2H,m), 7.35(5H, s), 7.4–7.8(1H,m), 7.78(1H,s), 8.04(1H,s).

Test 1: In vitro antifungal activity against *Candida albicans*

To each well of a 96-well microtiter plate, 75 μl of a dilute chemical solution adjusted with a 10% fetal bovine serum added MEM medium (containing glutamine and a carbonate salt) was poured, followed by the addition of 75 μl of 4×10$^4$ cells/ml of *C. albicans* ATCC 44859 suspended with the same medium. They were incubated at 37° C. for 20 hours in a CO$_2$ gas incubator. After incubation, morphological change of *C. albicans* was observed under an inverted microscope. The minimum chemical concentration permitting the apparent suppression of mycerial type growth compared with a control to which no chemical had been added was determined as a terminal point (ng/ml).

Test 2: In vitro antifungal activity against *Aspergillus fumigatus*

To each well of a 96-well microtiter plate, 100 μl of a dilute chemical solution adjusted with 0.165M MOPS-containing RPMI 1640 (containing glutamine and phenol red, carbonate-salt free; pH 7) were poured, followed by the addition of 100 μl of 6.0×10$^4$ cells/ml of an *A. fumigatus* IFM 40808 spore suspension in the same medium. They were incubated at 35° C. for 24 hours. After incubation, the minimum chemical concentration permitting the apparent suppression of mycerial type growth compared with a control to which no chemical had been added was determined as an MIC value (μg/ml).

Test 3: In vitro antifungal activity against *Aspergillus flavus*

To each well of a 96-well microtiter plate, 100 μl of a dilute chemical solution adjusted with 0.165M MOPS-containing RPMI 1640 (containing glutamine and phenol red, carbonate-salt free; pH 7) were poured, followed by the addition of 100 μl of 6.0×10⁴ cells/ml of an *A. flavus* IFM 41935 spore suspension in the same medium. They were incubated at 35° C. for 24 hours. After incubation, the minimum chemical concentration permitting the apparent suppression of mycerial type growth compared with a control to which no chemical had been added was determined as an MIC value (μg/ml).

TABLE 1

| Test compound | Terminal Point (ng/ml) C. albicans | MIC (μg/ml) A. fumigatus | A. flavus |
|---|---|---|---|
| Example 14 | 31.3 | 8 | 4 |
| Example 15 | 15.6 | 4 | 8 |
| Example 18 | 250 | 64 | 64 |
| Example 21 | 62.5 | 16 | 32 |
| Fluconazole | 250 | >128 | >128 |

Test 4: In vivo antifungal activity against *Candida albicans*

After 4-week-old, male, ICR (CRJ: CD-1) mouse was fasted for 6 hours, *C. albicans* IFM 40009 was inoculated to a tail vein of the mouse to give an amount of $3.0 \times 10^6$ cells/mouse, whereby infection was caused. A control group consisted of 8 mice, while a chemical-administered group consisted of 5 mice. The chemical was orally administered once an hour after the inoculation of the fungus and 24 hours after the inoculation, and once a day consecutively, four times in total, at 1.25 mg/kg each. The survival during 14 days after the infection was counted. In addition, the mean survival days of the control group and the mean survival days of the chemical-administered group were compared and statistically analyzed by the Kaplan-Meire method (Cox mantel test).

TABLE 2

| Test compound | Mean survival days | Survival mice on 14-th day |
|---|---|---|
| Example 20 | 14.0*** | 5/5 |
| Example 21 | 14.0** | 4/5 |
| Fluconazole | 9.6 | 0/5 |
| Control | 3.2 | 0/5 |

(vs. control *: $p < 0.001$, : $p < 0.01$)

Example 24

Tablets

TABLE 3

| Compound of Example 20 | 50 mg |
|---|---|
| Crystalline cellulose | 50 mg |
| Lactose | 50 mg |
| Hydroxypropyl cellulose | 18 mg |
| Magnesium stearate | 2 mg |
| Total | 170 mg |

In a manner known per se in the art, tablets having the above-described composition were prepared. The tablets can be formed as sugar coated tablets or film coated tablets as needed.

Example 25

Capsules

TABLE 4

| Compound of Example 20 | 50 mg |
|---|---|
| Soft silicic anhydride | 25 mg |
| Lactose | 100 mg |
| Starch | 50 mg |
| Talc | 25 mg |
| Total | 250 mg |

The above ingredients were filled in No. 1 capsules, whereby capsules were obtained.

Example 26

Granules

TABLE 5

| Compound of Example 20 | 50 mg |
|---|---|
| Lactose | 600 mg |
| Corn starch | 200 mg |
| Carboxymethyl cellulose sodium | 20 mg |
| Hydroxypropyl cellulose | 130 mg |
| Total | 1000 mg |

In a manner known per se in the art, granules having the above-described composition were prepared.

Example 27

Powders

TABLE 6

| Compound of Example 20 | 50 mg |
|---|---|
| Soft silicic anhydride | 20 mg |
| Precipitated calcium carbonate | 10 mg |
| Lactose | 250 mg |
| Starch | 70 mg |
| Total | 400 mg |

In a manner known per se in the art, powders having the above-described composition were prepared.

Example 28

Injection

TABLE 7

| Compound of Example 20 | 5 mg |
|---|---|
| Hydrogenated castor oil | 85 mg |
| Propylene glycol | 60 mg |
| Glucose | 50 mg |
| Distilled water for injection | q.s. |
| Total | 1 ml |

In a manner known per se in the art, an injection having the above-described composition was prepared.

Example 29

Intravenous Drip Infusion

TABLE 8

| | |
|---|---|
| Compound of Example 20 | 50 mg |
| Hydrogenated castor oil | 5 g |
| Propylene glycol | 10 mg |
| Glucose | 14.5 mg |
| Distilled water for injection | q.s. |
| Total | 100 ml |

An intravenous drip infusion having the above-described composition was prepared in a manner known per se in the art.

What is claimed is:

1. A triazole derivative represented by formula (1):

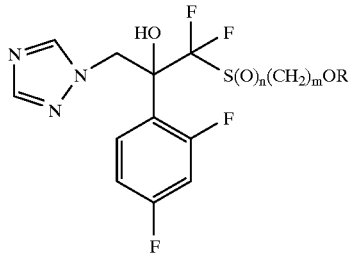

wherein R represents hydrogen, straight or branched $C_{1-10}$ alkyl group, a $C_{7-11}$ aralkyl group or a $C_{2-10}$ carboacyl group, n stands for 0 to 2 and m stands for 1 to 5; or a salt thereof.

2. A pharmaceutical composition, comprising:
a pharmaceutically effective amount of the compound of claim 1 in combination with a pharmaceutically acceptable excipient.

3. A pharmaceutical composition according to claim 2, which is a mycocide composition.

4. A triazole derivative represented by formula (I):

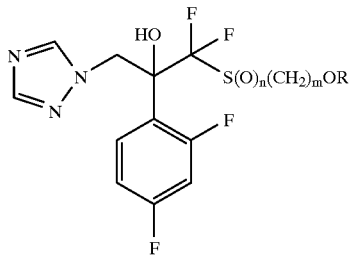

wherein R represents hydrogen, a straight or branched $C_{1-10}$ alkyl group, a $C_{7-11}$ aralkyl group or a $C_{2-10}$ acyl group, n is 1 or 2 and m is an integer of 1–5; or a salt thereof.

5. A method of treating a subject suffering from a mycotic infection, which comprises:
administering to said subject an effective amount of a triazole derivative or salt thereof as claimed in claim 1.

6. The triazole derivative according to claim 1, wherein said $C_{1-10}$ alkyl group is methyl, ethyl, n-propyl, isopropyl, n-butyl, tert-butyl, pentyl, hexyl, octyl or decyl.

7. The triazole derivative according to claim 1, wherein said $C_{7-11}$-aralkyl is phenyl-$C_{1-5}$-alkyl.

8. The triazole derivative according to claim 1, wherein said $C_{2-10}$ carboacyl group is $C_{2-10}$ alkanoyl or $C_{7-10}$ aroyl.

* * * * *